US009121550B2

(12) United States Patent
Ong et al.

(10) Patent No.: US 9,121,550 B2
(45) Date of Patent: Sep. 1, 2015

(54) APPARATUS OF A MAGNETIC RESONANCE MULTIPHASE FLOW METER

(75) Inventors: Joo Tim Ong, Houston, TX (US); Terry R. Bussear, Spring, TX (US); Carl M. Edwards, Katy, TX (US); Graeme S. Young, The Woodlands, TX (US)

(73) Assignee: Baker Hughes Incorporated, Houston, TX (US)

( * ) Notice: Subject to any disclaimer, the term of this patent is extended or adjusted under 35 U.S.C. 154(b) by 379 days.

(21) Appl. No.: 13/180,902

(22) Filed: Jul. 12, 2011

(65) Prior Publication Data
US 2013/0018602 A1    Jan. 17, 2013

(51) Int. Cl.
| | |
|---|---|
| *G01F 1/58* | (2006.01) |
| *F17D 5/02* | (2006.01) |
| *G01F 1/716* | (2006.01) |
| *G01F 1/74* | (2006.01) |
| *G01R 33/383* | (2006.01) |
| *G01R 33/563* | (2006.01) |
| *G01R 33/00* | (2006.01) |
| *G01N 24/08* | (2006.01) |

(52) U.S. Cl.
CPC .. *F17D 5/02* (2013.01); *G01F 1/58* (2013.01); *G01F 1/716* (2013.01); *G01F 1/74* (2013.01); *G01R 33/383* (2013.01); *G01R 33/56308* (2013.01); *G01N 24/081* (2013.01); *G01R 33/0047* (2013.01)

(58) Field of Classification Search
CPC ............. G01F 1/58; G01F 1/74; G01F 1/716; F17D 5/02; G01R 33/0047; G01R 33/383; G01R 33/56308; G01N 24/081
See application file for complete search history.

(56) References Cited

U.S. PATENT DOCUMENTS

| | | | |
|---|---|---|---|
| 4,782,295 A | 11/1988 | Lew | |
| 5,531,126 A * | 7/1996 | Drahm | 73/861.357 |
| 6,002,317 A | 12/1999 | Pignataro | |
| 6,229,422 B1 | 5/2001 | Pignataro | |
| 6,789,432 B2 * | 9/2004 | Guazzoni et al. | 73/861.12 |
| 6,794,864 B2 | 9/2004 | Mirotchnik et al. | |
| 7,298,142 B2 * | 11/2007 | Hursan et al. | 324/303 |

(Continued)

FOREIGN PATENT DOCUMENTS

| | | | | |
|---|---|---|---|---|
| JP | 07308677 A | * | 11/1995 | C02F 1/48 |
| WO | WO2008013789 A2 | | 1/2008 | |

OTHER PUBLICATIONS

International Search Report and Written Opinion dated Dec. 3, 2012 for International Application No. PCT/US2012/040101; all references in PCT are cited above.

*Primary Examiner* — Mohamed Charioui
*Assistant Examiner* — John Kuan
(74) *Attorney, Agent, or Firm* — Cantor Colburn LLP

(57) ABSTRACT

An apparatus and method for estimating a parameter of a fluid flowing in a tubular is disclosed. A source of a primary magnetic field is coupled to the tubular and is configured to induce the primary magnetic field in the fluid to align nuclei of the fluid in the tubular along the primary magnetic field. A transmitter transmits an excitation signal into the fluid. A receiver detects a signal from the aligned nuclei responsive to the excitation signal. A processor estimates the parameter of the fluid from the detected signal. The source of the primary magnetic field is removable from the tubular. A coil may induce a secondary magnetic field to either enhance the strength of the primary magnetic field in the tubular or substantially cancel the primary magnetic field in the tubular, for example, to reduce particle build-up in the tubular.

19 Claims, 17 Drawing Sheets

(56) References Cited

U.S. PATENT DOCUMENTS

| | | | |
|---|---|---|---|
| RE40,167 E * | 3/2008 | Edwards et al. | 324/303 |
| 7,501,819 B2 | 3/2009 | Ong | |
| 7,683,613 B2 | 3/2010 | Freedman et al. | |
| 8,248,067 B2 * | 8/2012 | Ong | 324/303 |
| 2004/0239460 A1 | 12/2004 | Kocijan | |
| 2005/0017715 A1 * | 1/2005 | Prammer et al. | 324/303 |
| 2006/0174716 A1 * | 8/2006 | Zajac et al. | 73/861.12 |
| 2006/0185442 A1 * | 8/2006 | Keese et al. | 73/861.12 |
| 2006/0255799 A1 | 11/2006 | Reiderman | |
| 2007/0068862 A1 * | 3/2007 | Sisemore | 210/222 |
| 2007/0215342 A1 * | 9/2007 | Fincher et al. | 166/65.1 |
| 2007/0222444 A1 | 9/2007 | Reiderman | |
| 2009/0157315 A1 | 6/2009 | Ong | |
| 2009/0260453 A1 * | 10/2009 | Kawakami et al. | 73/861.12 |
| 2010/0313958 A1 * | 12/2010 | Patel et al. | 137/1 |
| 2011/0001474 A1 * | 1/2011 | Miller et al. | 324/306 |

* cited by examiner

APPARATUS OF A MAGNETIC RESONANCE MULTIPHASE FLOW METER

BACKGROUND OF THE DISCLOSURE

1. Field of the Disclosure

The present disclosure is related to an apparatus for estimating a parameter of a fluid flowing in a tubular and in particular to a removable apparatus that may be coupled to the tubular at various locations.

2. Description of the Related Art

In the oil and gas industry it has become increasing important in recent years to obtain accurate measurements of one or more parameters of fluids flowing through a tubular, such as fluids produced by drilling operations. Current exemplary measurement devices for determine these parameters include Nuclear Magnetic Resonance (NMR) and Electronics Spin Resonance (ESR) analysis. Typically, the measurement device and its components are built into a section of the tubular designed for this purpose. The measurement device therefore is a permanent fixture of the tubular. However, operations may require determining fluid parameters at multiple locations of the tubular or at various tubular branches. Building measurement device at each location can become cumbersome and expensive. Therefore, the present disclosure provides a measurement device that can be applied at various locations of a tubular to determine a parameter of a fluid flowing therein.

SUMMARY OF THE DISCLOSURE

In one aspect, the present disclosure provides an apparatus for estimating a parameter of a fluid flowing in a tubular, including: a source of a primary magnetic field coupled to the tubular and configured to induce the primary magnetic field in the fluid to align nuclei of the fluid in the tubular along the primary magnetic field; a transmitter configured to transmit an excitation signal into the fluid; a receiver configured to detect a signal from the aligned nuclei responsive to the excitation signal; and a processor configured to estimate the parameter of the fluid from the detected signal.

In another aspect, the present disclosure provides a method of estimating a parameter of a fluid flowing in a tubular, including: coupling a source of a primary magnetic field to the tubular to induce the primary magnetic field in the fluid to align nuclei of the fluid in the tubular along the primary magnetic field; transmitting an excitation signal into the flowing fluid; detecting a signal from the aligned nuclei responsive to the excitation signal; and estimating the parameter of the fluid from the detected response signal.

In yet another aspect, the present disclosure provides a device for estimating a parameter of a fluid flowing in a tubular, including a first permanent magnet configured to couple to the tubular to induce a primary magnetic field in the fluid to align nuclei of the fluid along a direction of the primary magnetic field for estimating the parameter of the fluid.

Examples of certain features of the apparatus and method disclosed herein are summarized rather broadly in order that the detailed description thereof that follows may be better understood. There are, of course, additional features of the apparatus and method disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, in which like elements have been given like numerals and wherein.

DETAILED DESCRIPTION OF THE DISCLOSURE

Figure 1:
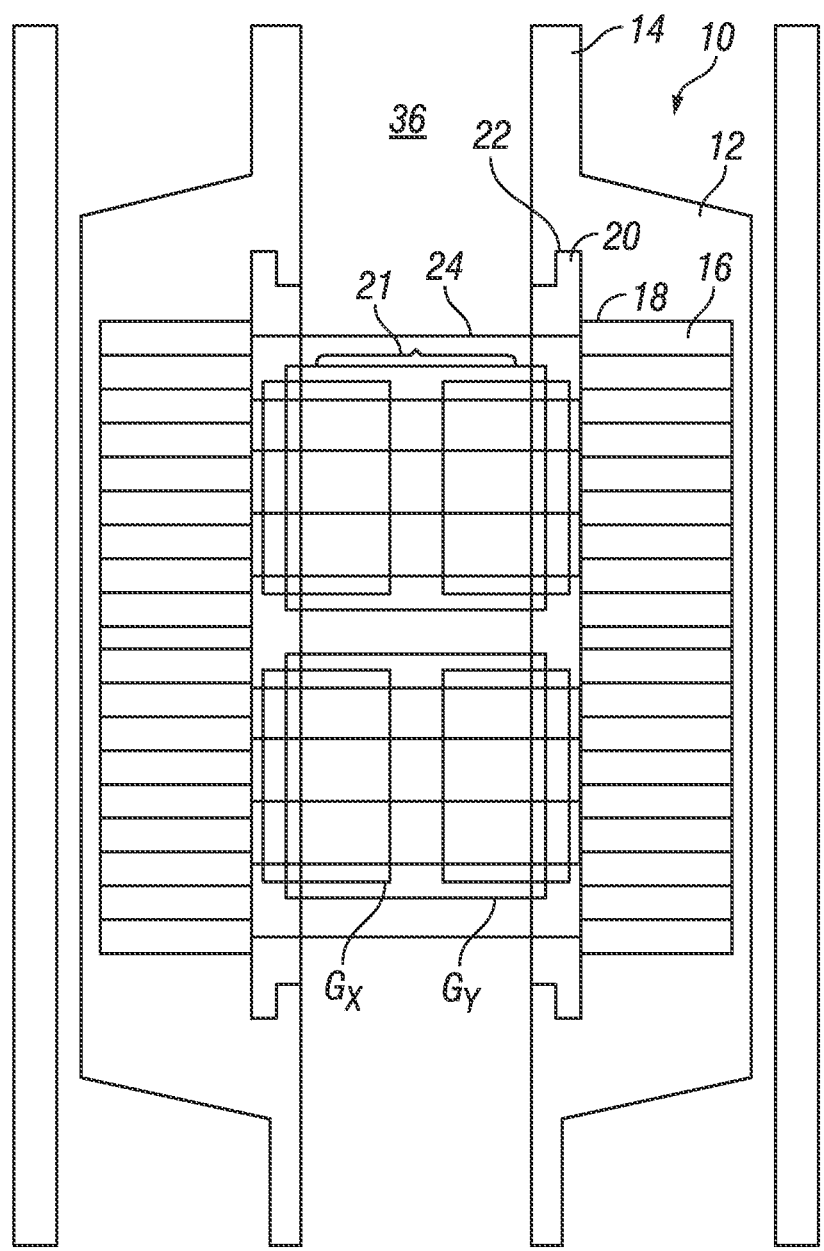
FIG. 1 is a transverse side view of a first embodiment of the apparatus according to the present invention.
Figure 1A:
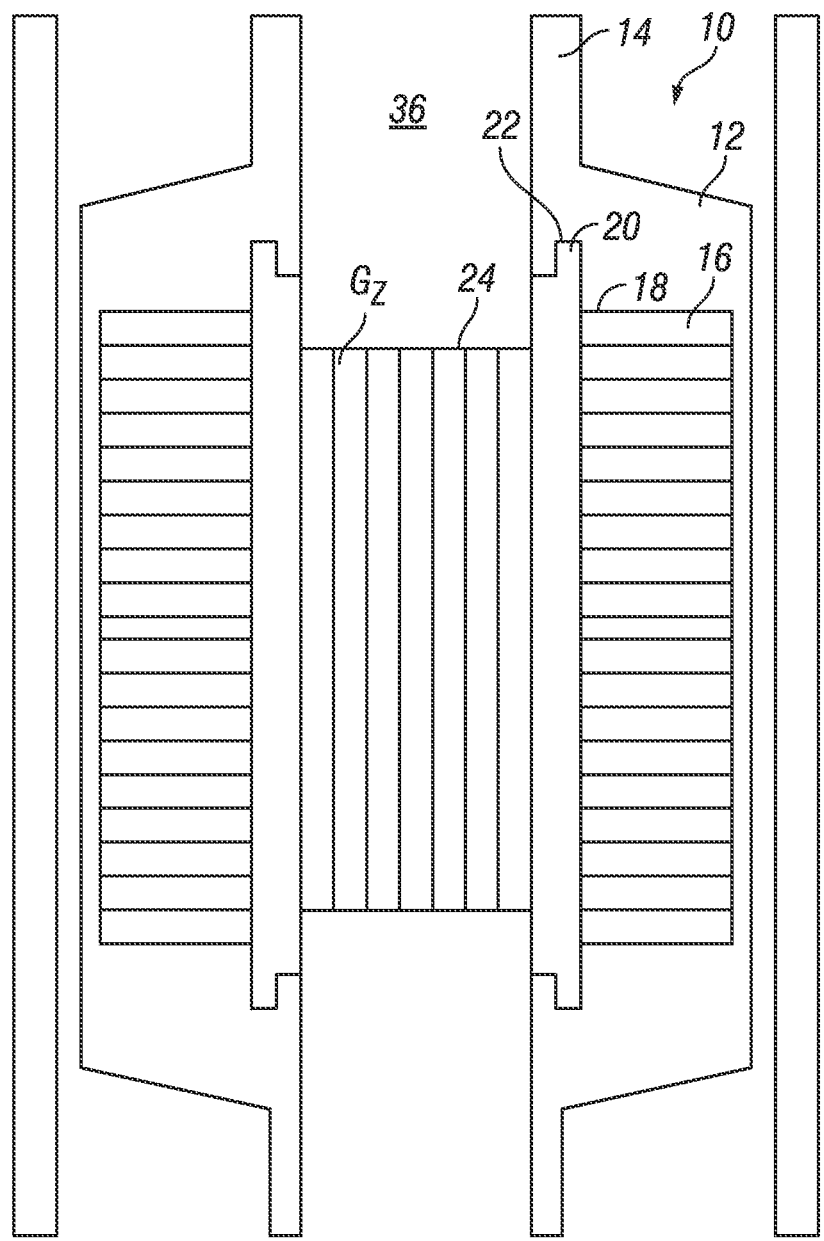
FIG. 1A is a transverse side view of the apparatus of FIG. 1 showing magnetic gradient coils which act in the direction of the z-axis with respect to the reference axes indicated on FIG. 1.
Figure 2:
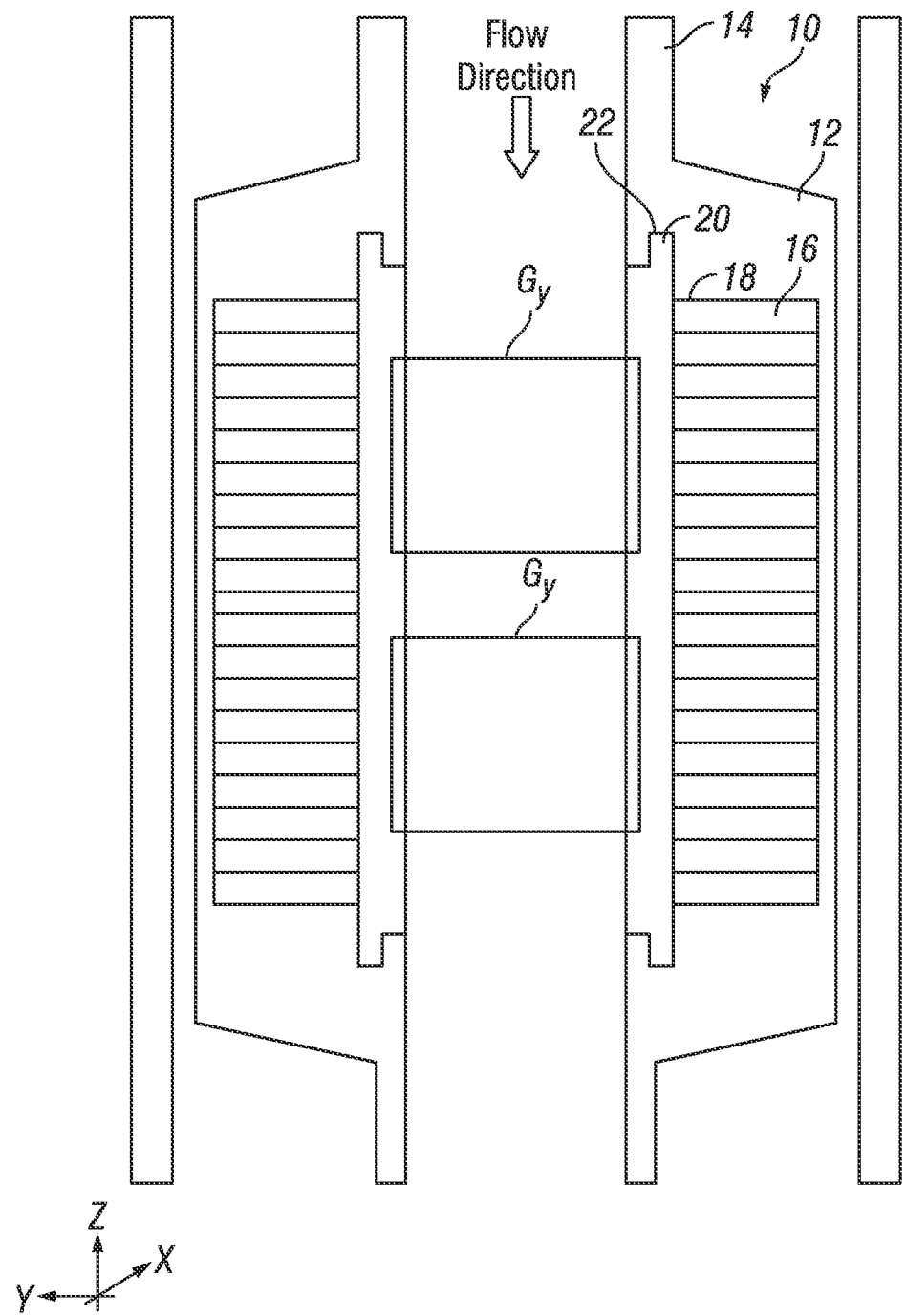
FIG. 2 is a transverse side view of the apparatus of FIG. 1 showing magnetic gradient coils which act in the direction of the y-axis with respect to the reference axes indicated on FIG. 1.
Figure 3:
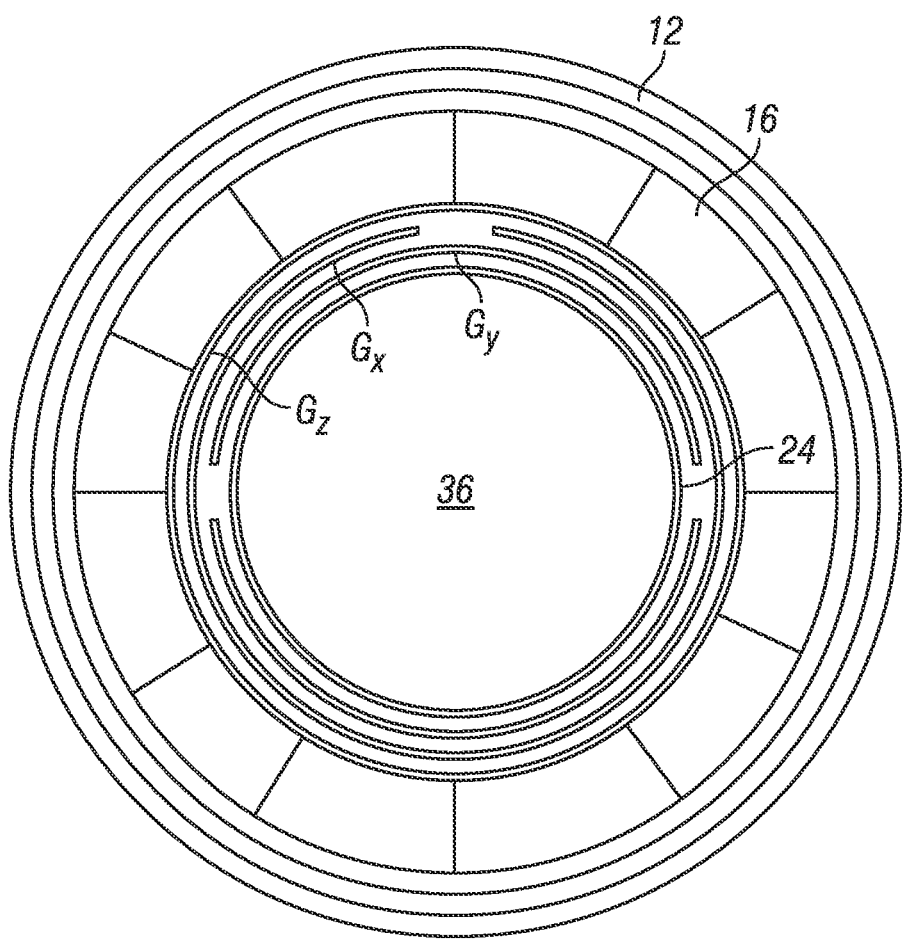
FIG. 3 is a cross sectional view of the apparatus of FIG. 1 showing the components of the magnetic gradient coils which act in the x, y and z directions with respect to the reference axes indicated on FIG. 1.
Figure 4:
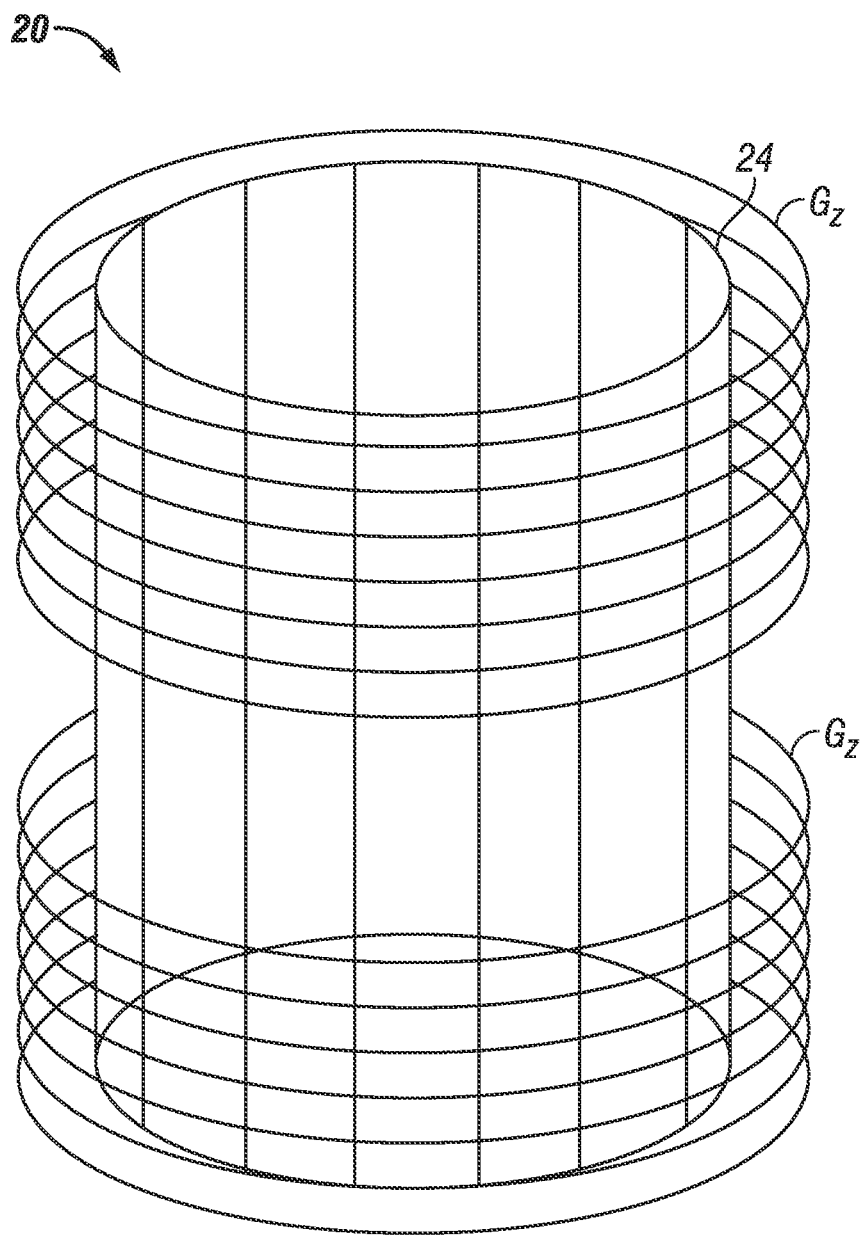
FIG. 4 is a schematic view of the component of the gradient coils which act in the z-axis direction with respect to the reference axes of FIG. 1, arranged around combined transmission and reception coils in accordance with the first embodiment of the present invention.
Figure 5:
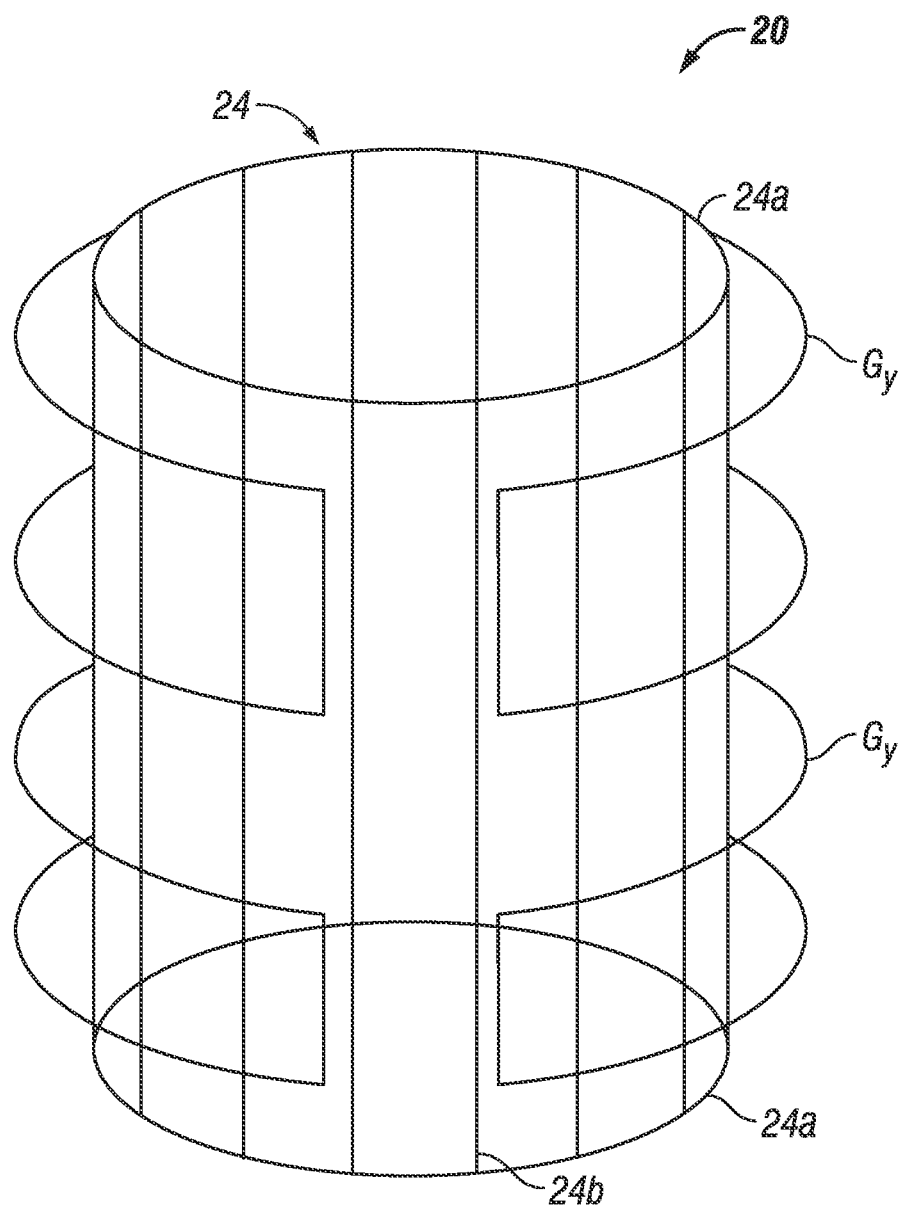
FIG. 5 is a schematic view of the gradient coils which act in the y-axis direction with respect to the reference axes of FIG. 1, arranged around combined transmission and reception coils in accordance with the first embodiment of the present invention.

Referring to FIG. 1 the apparatus 10 in accordance with the first embodiment of the present invention comprises an outer housing 12 which surrounds a section of a fluid flow pipe 14, such as production tubing, by locking thereto via a suitable locking mechanism. Inside the housing 12 is located a primary permanent magnet 16 in an outermost recess 18 and a secondary electromagnet housing 20 located in an innermost recess 22. The electromagnet housing 20 has located within it an electromagnet 21 which comprises electromagnet coils Gx, Gy and (as shown in FIG. 1A) Gz. Combined transmission and reception coils 24 are also provided within the inner diameter of the electromagnet housing 20.

Outer housing 12 provides magnetic shielding which substantially minimizes leakage of magnetic field outside the apparatus 10, and provides safe handling of the tool. This also improves the signal transmission and reception performance of the coils 24 by minimizing interference from surrounding radio signals such as FM radio signals. Housing 12, in the present embodiment, comprises low permeability iron, (typically $\mu r<1.00$) which provides the main outer body of the apparatus. The material is typically around 10 mm thick around the mid portion of the apparatus 10 and thicker toward the ends of the apparatus 10, typically up to a thickness of around 60 mm. The skilled reader will realize that different thickness and material may be used in the housing 12 in order to suit the particular application.

Figure 6:
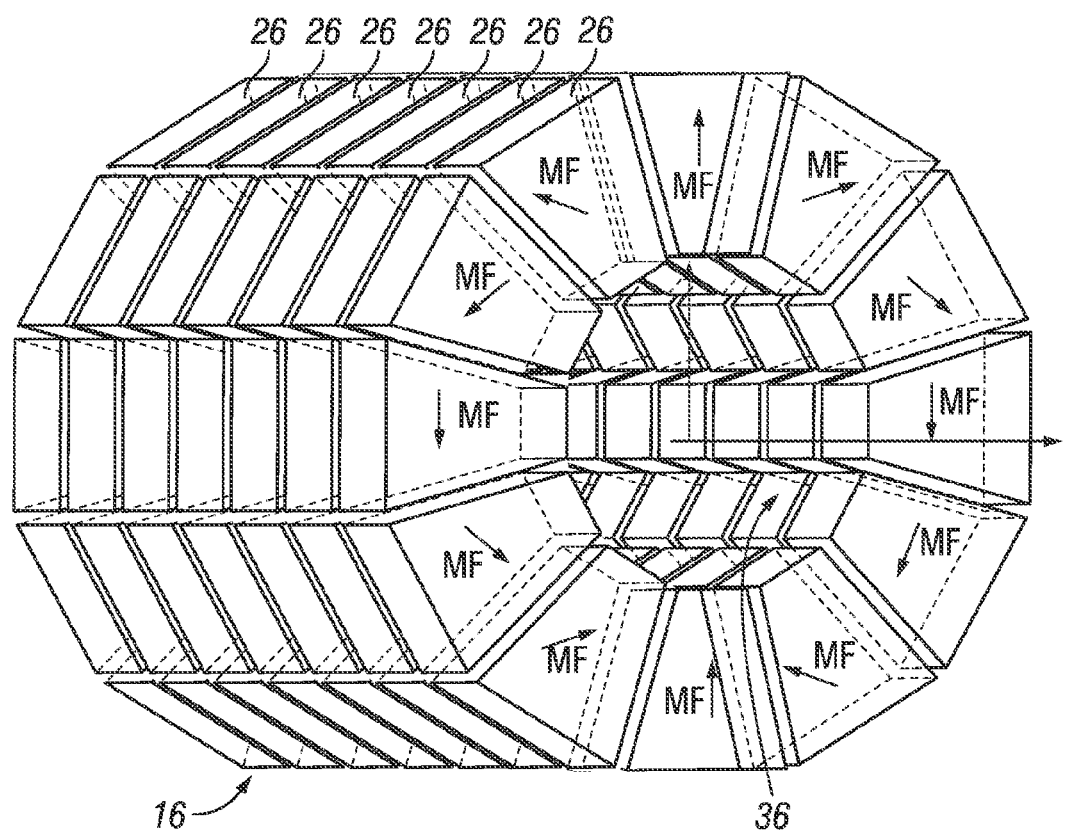
FIG. 6 is an illustration of the preferred magnetic field orientation in order to produce the homogeneous magnet used in accordance with the present invention.
Figure 8:
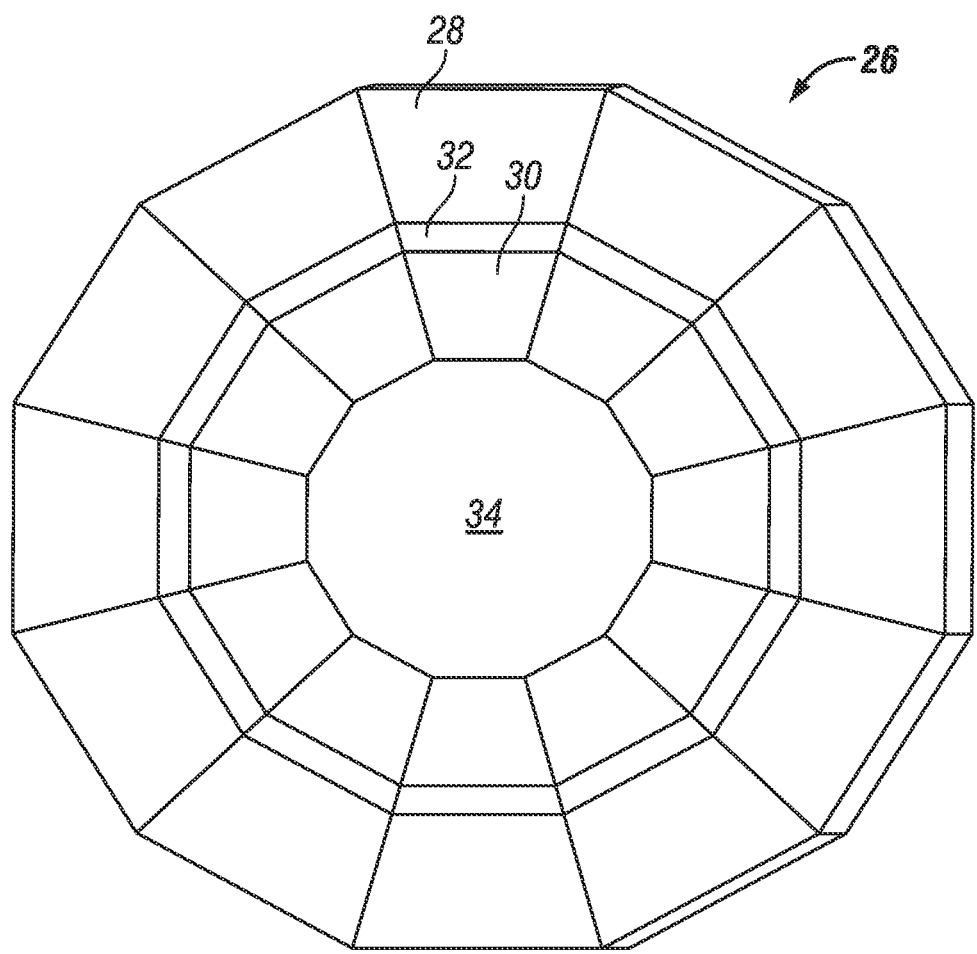
FIG. 8 is a schematic cross sectional diagram of the primary magnet composition used in accordance with the present invention.
Figure 9:
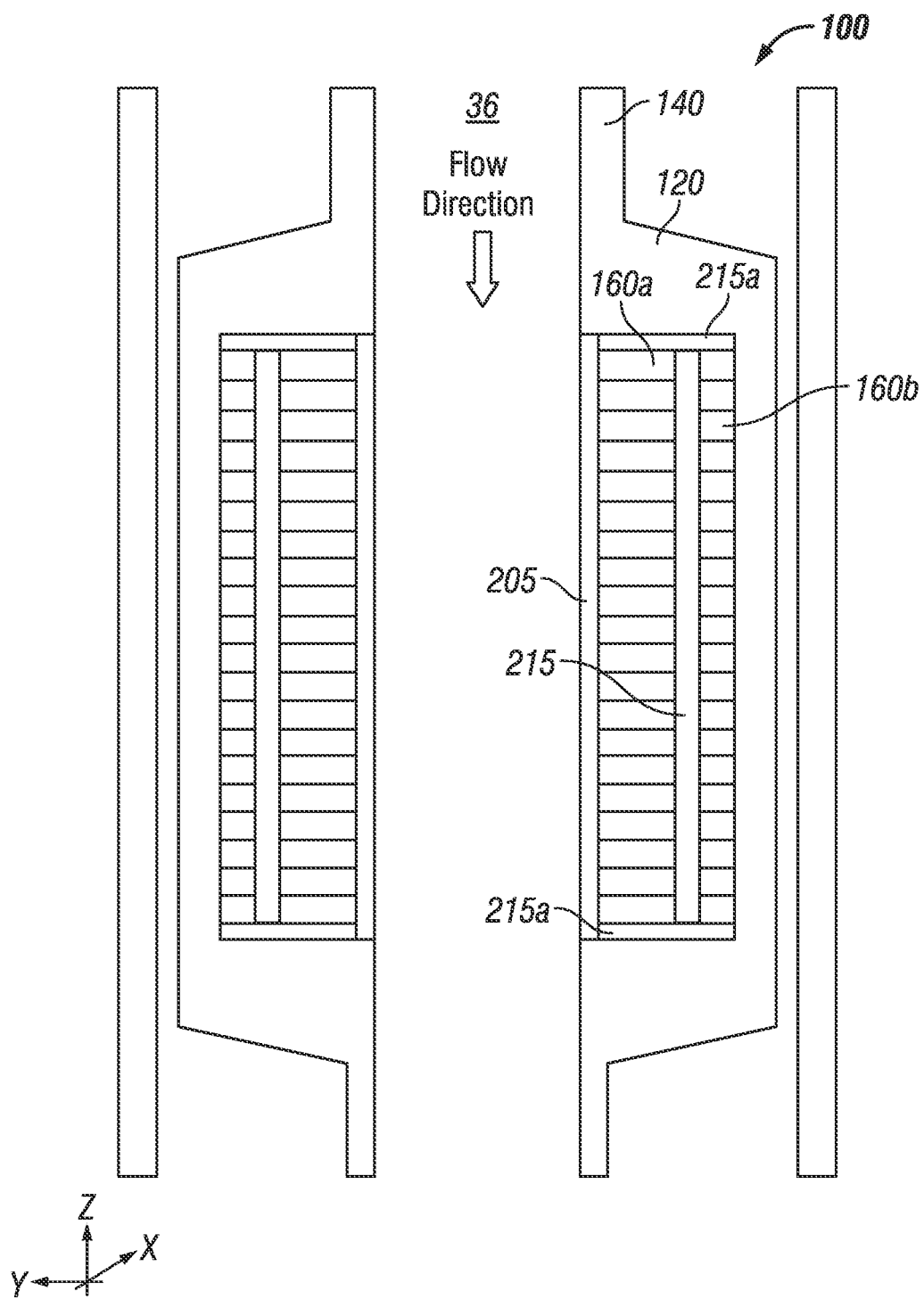
FIG. 9 is a transverse side view of a second embodiment of the apparatus according to the present invention without the gradient and transmission coils shown.

Referring particularly to FIGS. 6 and 8, the primary permanent magnet 16 comprises a number of concentrically arranged magnetic cells 26 which are stacked together. Each magnetic cell 26 comprises a number of outer segments 28 (FIG. 8) arranged adjacent a number of inner segments 30 such that a circumferential band of inner segments 30 are arranged within a circumferential band of outer segments 28. Flat plates 32 are positioned between the circumferential band of outer segments 28 and the circumferential band of inner segments 30 such that a circumferential band of plates 32 is located between the outer segments 28 and the inner segments 30. The plates 32 are typically formed of an iron based material having a permeability of greater than 1000.

Aperture 34 is provided in the centre of each cell 26 to allow the flow of fluid therethrough as will be discussed subsequently. When the cells 26 are stacked together they form a throughbore 36 (as shown in FIG. 6) along the length of the magnet 16. The flat plates 32 ensure that the resultant magnetic field produced by inner segments 30 and outer segments 28 is focused toward the center of the aperture 34 of each cell and hence along the throughbore 36 of the apparatus 10.

The skilled reader will understand that the term permanent magnet in this context is taken to mean a magnet which provides a constant magnetic field without requiring, for example, an electric current in order to create the magnetic field. In an alternative embodiment, the permanent magnet may be an electromagnet which provides a continuous and substantially homogeneous magnetic field.

The direction of the magnetic field vectors (indicated by MF in FIG. 6) of each outer 28 and inner 30 segment is carefully arranged during manufacture in order to create a resultant magnetic field for the magnet 16 which is as close to being homogeneous as possible throughout the throughbore of the magnet 16. This ensures that the magnetic field present within the throughbore 36 of the magnet 16 remains consistent within the throughbore 36 irrespective of the location within the throughbore 36 that the magnetic field is experienced. Typically, the required homogeneity is in the region of around 1.0 ppm. This ensures accurate measurements are possible using the apparatus 10 in conjunction with the NMR techniques as will be discussed subsequently.

The secondary electromagnet housing 20 is provided with a combined transmission and reception coil 24 which is capable of both transmitting a radio frequency pulse and detecting the radio frequency emitted by nuclei excited by such a radio frequency pulse. In the embodiment shown in the Figures, the coil 24 comprises a pair of circular loops 24a at the top and bottom of the coil 24 connected by circumferentially spaced connecting coils 24b to form a "birdcage" configuration. This provides the apparatus 10 with the ability to both transmit a radio frequency pulse evenly throughout the throughbore 36 and competently detect radio frequency signals emitted by nuclei at any location within the throughbore 36 of the apparatus 10. Rather than a "birdcage" configuration the coils may alternatively be arranged to provide a "saddle coil" configuration depending upon the application.

Figure 7A:
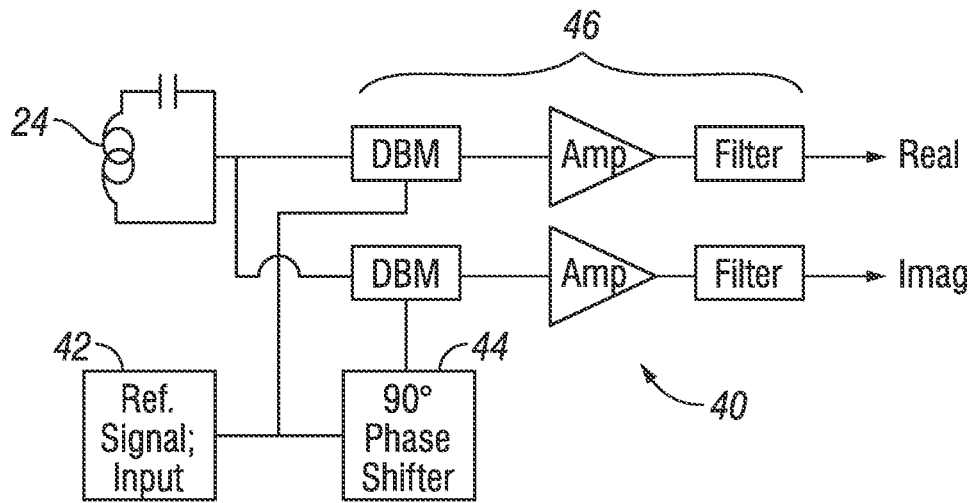
FIG. 7A is a schematic circuit diagram showing the interaction between the various components of the receiving circuit of the combined receiving and transmission coils.
Figure 7B:
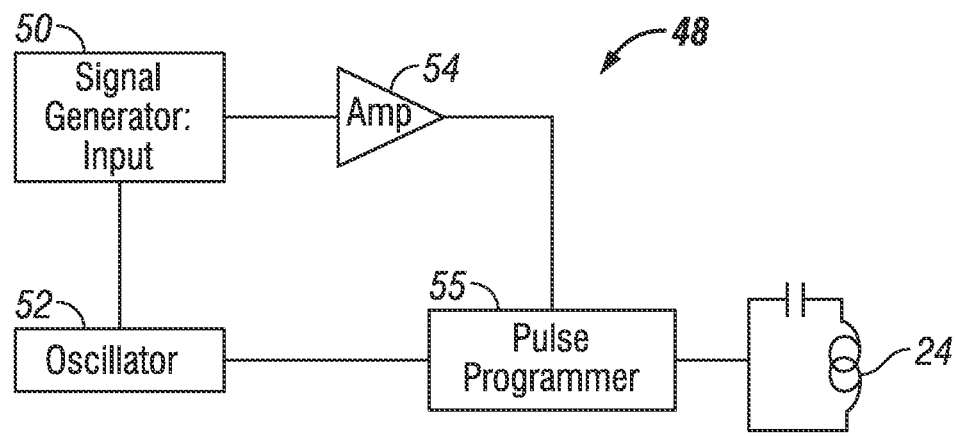
FIG. 7B is a schematic circuit diagram showing the interaction between the various components of the transmitting circuit of the combined receiving and transmission coils.

Referring to FIG. 7A, the receiver circuit 40 of the combined transmission and reception coils 24 comprises a reference signal input generator 42 and a 90 .degree phase shifter 44 connected to a standard amplification and filtering system 46 in order to provide a real and imaginary output signal as a result of the signal received from the coil 24. Referring to FIG. 7B, the transmitter circuit 48 of the combined transmission and reception coils 24 comprises a signal generator input module 50 and an oscillator 52 which are linked to an amp 54 and a pulse programmer 55 in order to transmit the required radio frequency through coil 24. Though illustrated separately in FIGS. 7A and 7B, it will be understood that these circuits may be combined or integrated in order to provide the required transmission and reception capability of combined transmission and reception coils 24.

The secondary electromagnet housing 20 provides the magnetic gradient using coils Gx, Gy, and Gz which selectively (depending upon whether the electromagnet is on or off) provide a graduated magnetic field within the throughbore 36 of the apparatus in the x, y, and z directions respectively indicated by the reference axes R in FIG. 1. This arrangement provides the graduated magnetic field required by the flow rate calculation process described subsequently.

The profile of both the primary permanent magnet 16 and the secondary electromagnet 20 are arranged in the present embodiment, such that they can be housed within the outermost recess 18 and innermost recess 22 respectively in order to maintain a consistent diameter of throughbore 36 through the apparatus 10 such that disturbance of the fluid flowing from the pipe 14 through the apparatus 10 is minimized.

A second embodiment of the present invention having a number of modifications will now be described. Many components of the second embodiment are the same as those described in relation to the first embodiment. Such components will not be described any further. In addition, a number of components in the second embodiment correspond to similar components previously described in relation to the first embodiment, and where this applies, similar reference numerals will be used.

Referring to FIGS. 9 to 13, the apparatus 100 in accordance with the second embodiment of the present invention comprises a fluid flow pipe 140 and an outer housing 120 surrounding a primary magnet 160. Primary magnet 160 has an inner ring 160a and an outer ring 160b. A secondary electromagnet is provided in housing 205 as discussed subsequently. Transmission/reception coil housing 205 is provided on the internal bore of the apparatus 100. The housing 205 may be made of a material such as Poly-Ether-Ether-Ketone (PEEK) or a nickel alloy such as Inconel®. The required pressure rating using (PEEK) is generally achieved using a housing 205 having a very thick wall (in the region of 20 mm). Such a wall generally degrades the magnetic field strength at the center of the flow path since magnet strength decreases with radial distance from the magnet. The thickness required using Inconel® is much less (in the region of 7 mm). In addition, the use of Inconel® (which has permeability comparable with free space ($\mu r \cong 1$)), concentrates the magnetic field into the flow path, thereby increasing the magnetic strength homogeneity.

The housing 205 in the present embodiment is provided with recessed tracks (not shown) which are machined onto the outer surface of the housing 205 during manufacture. Additional shapes may also be machined onto the outer surface in order to accommodate components such as the transmission and reception coil capacitors used in the transmission and reception circuit. Electrical insulation (not shown) such as adhesive insulant is also provided between the transmission/reception coil and the housing 205.

Figure 10:
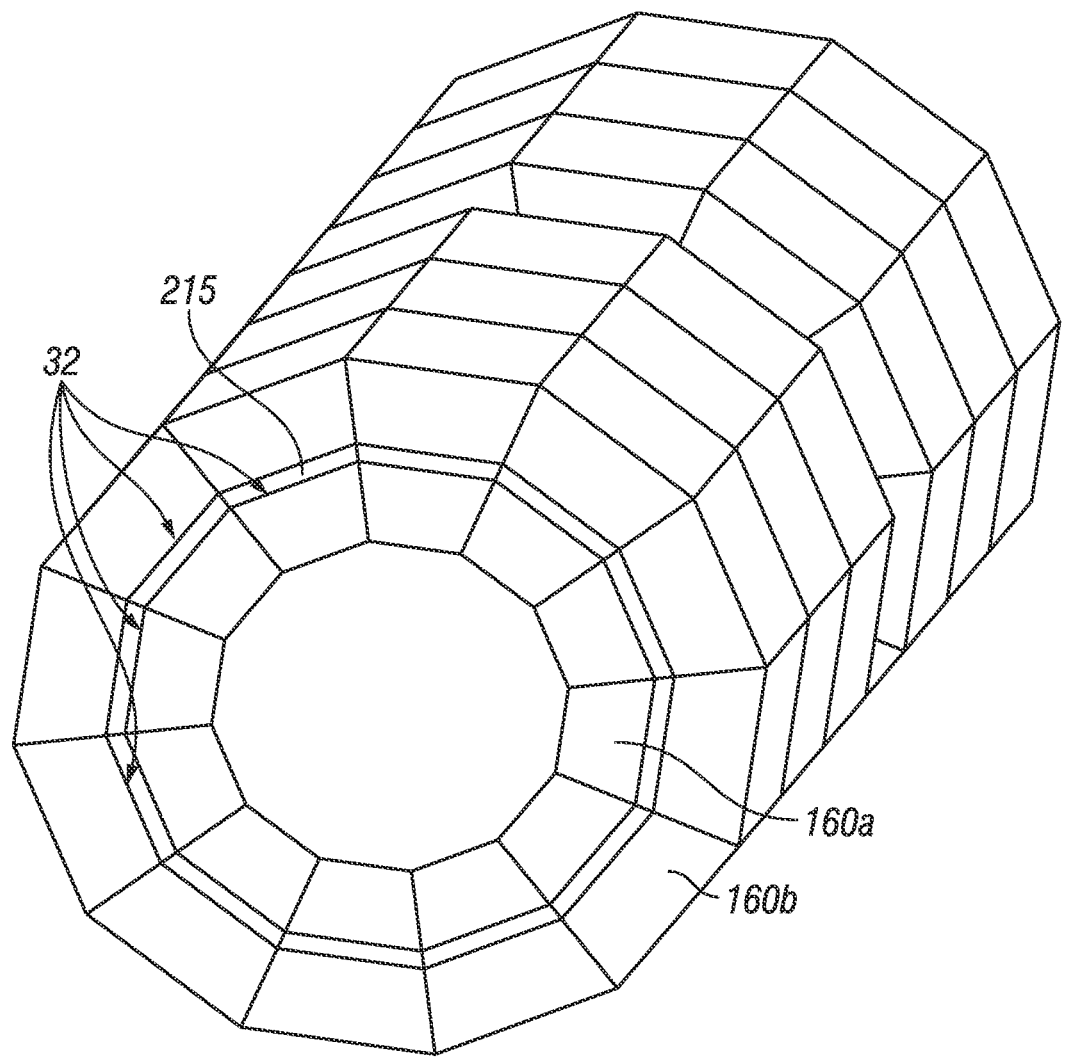
FIG. 10 is a schematic perspective view of the magnet configuration used in the apparatus of FIG. 9.
Figure 11:
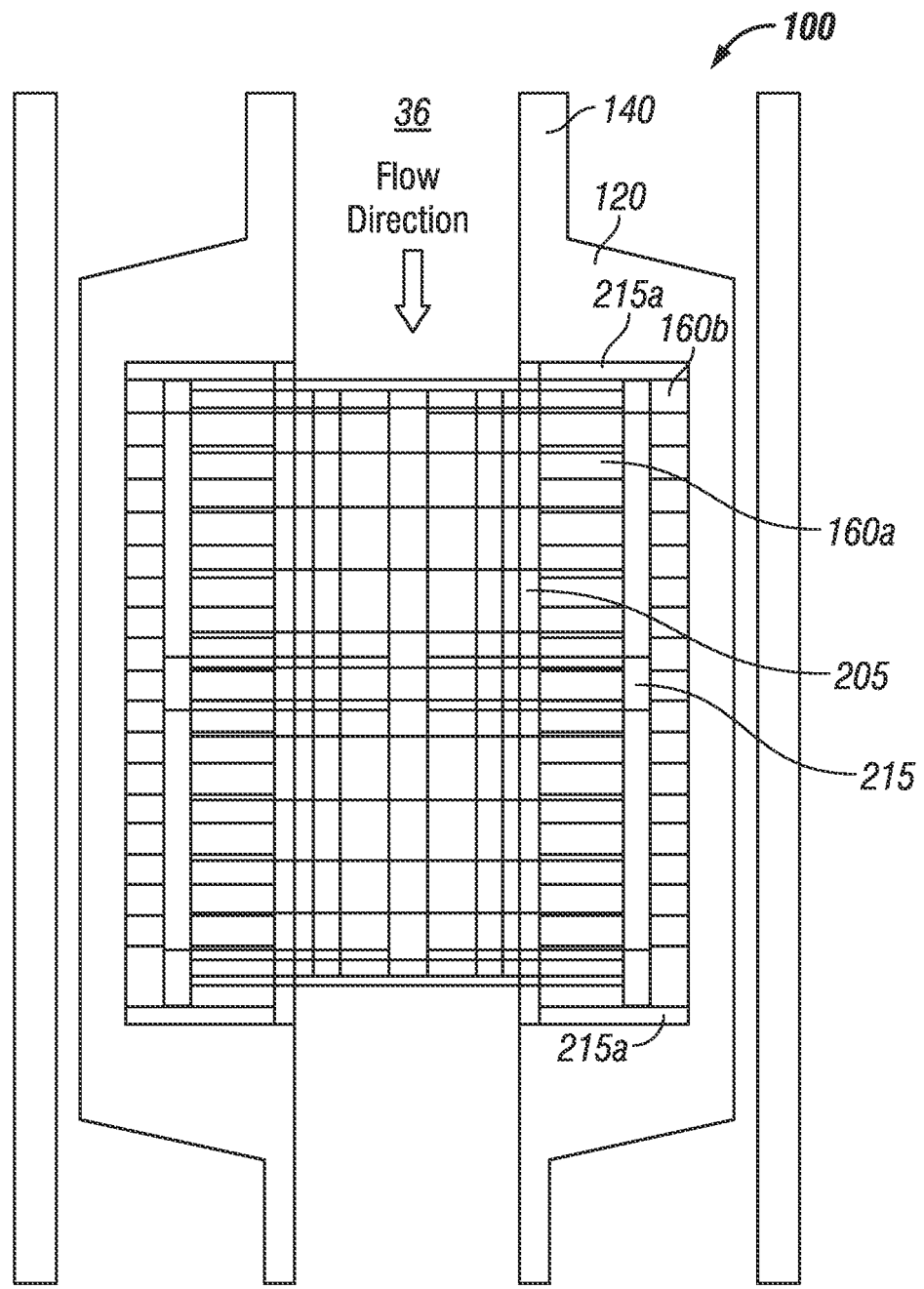
FIG. 11 is a transverse side view of the apparatus of FIG. 9 showing the gradient and transmission coils.

In further contrast, with the first embodiment, the apparatus 100 has gradient coils Gx, Gy, Gz mounted in tubing 215 between the primary magnet portions 160a and 160b. This separates the magnets 160a and 160b from one another which increases the combined efficiency of the magnets in producing a high strength homogeneous magnetic field in the flow path. The tubing 215 also provides mechanical support to retain the primary magnet and to provide support against the pressure exerted from the flow. In the present embodiment, the tubing 215 is made from high permeability iron and is dodecagonal in shape (as shown in FIG. 10). A pair of axial end members 215a are also provided in order to provide a magnetically permeable path for the magnetic field.

Figure 12:
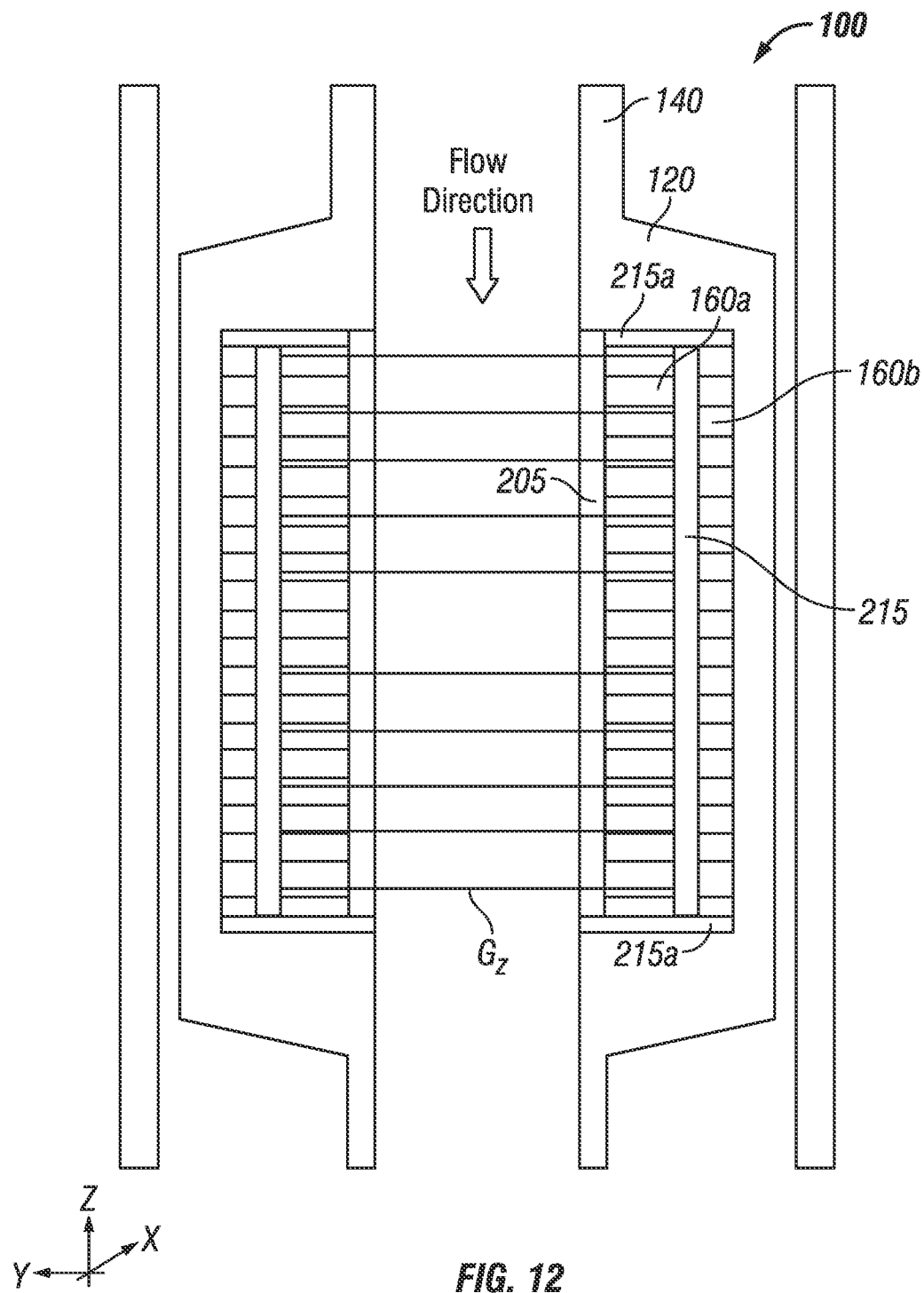
FIG. 12 is a schematic view of the component of the gradient coils of FIG. 10 which act in the z-axis direction.
Figure 13:
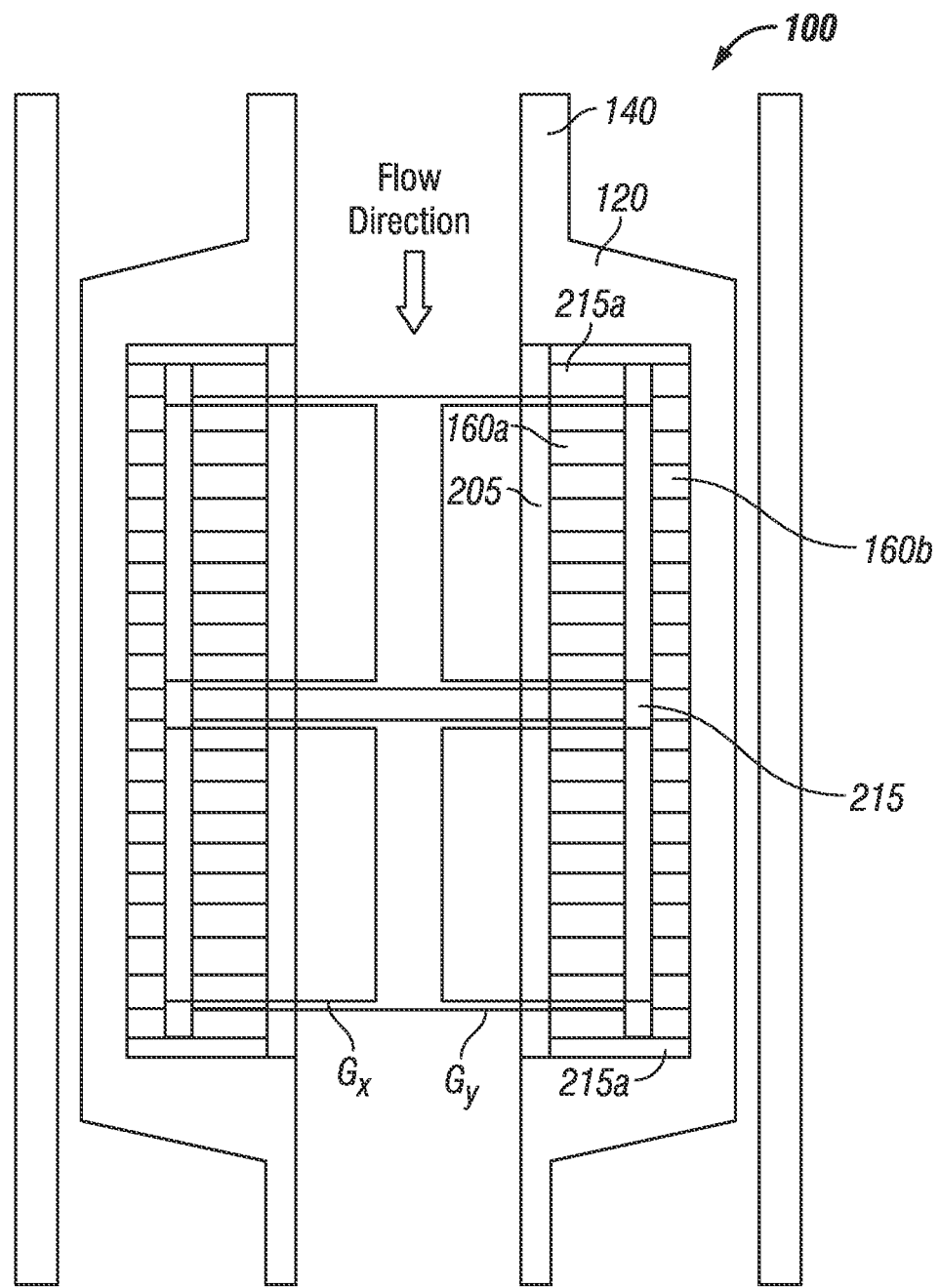
FIG. 13 is a schematic view of the component of the gradient coils of FIG. 10 which act in the x and y-axis directions.

As seen in FIG. 12, tubing 215 houses the axial gradient coil along the flow path (Gz) on the inner surface and the orthogonal gradients (Gx and Gy) on the outer surface (see FIG. 13). Again, these coils are provided in recessed tracks on the tubing 215 and are insulated from the tubing itself using adhesive insulant. The gradient coils are capable of imparting a variable magnetic field as discussed subsequently and in this regard can be considered as an electromagnet.

The tubing 215 is provided with a tubular inner diameter in order to provide minimal frictional losses to the fluid passing therethrough, and a dodecagonal outer surface which allows the tubing to fit within the rings of magnets.

Figure 14:
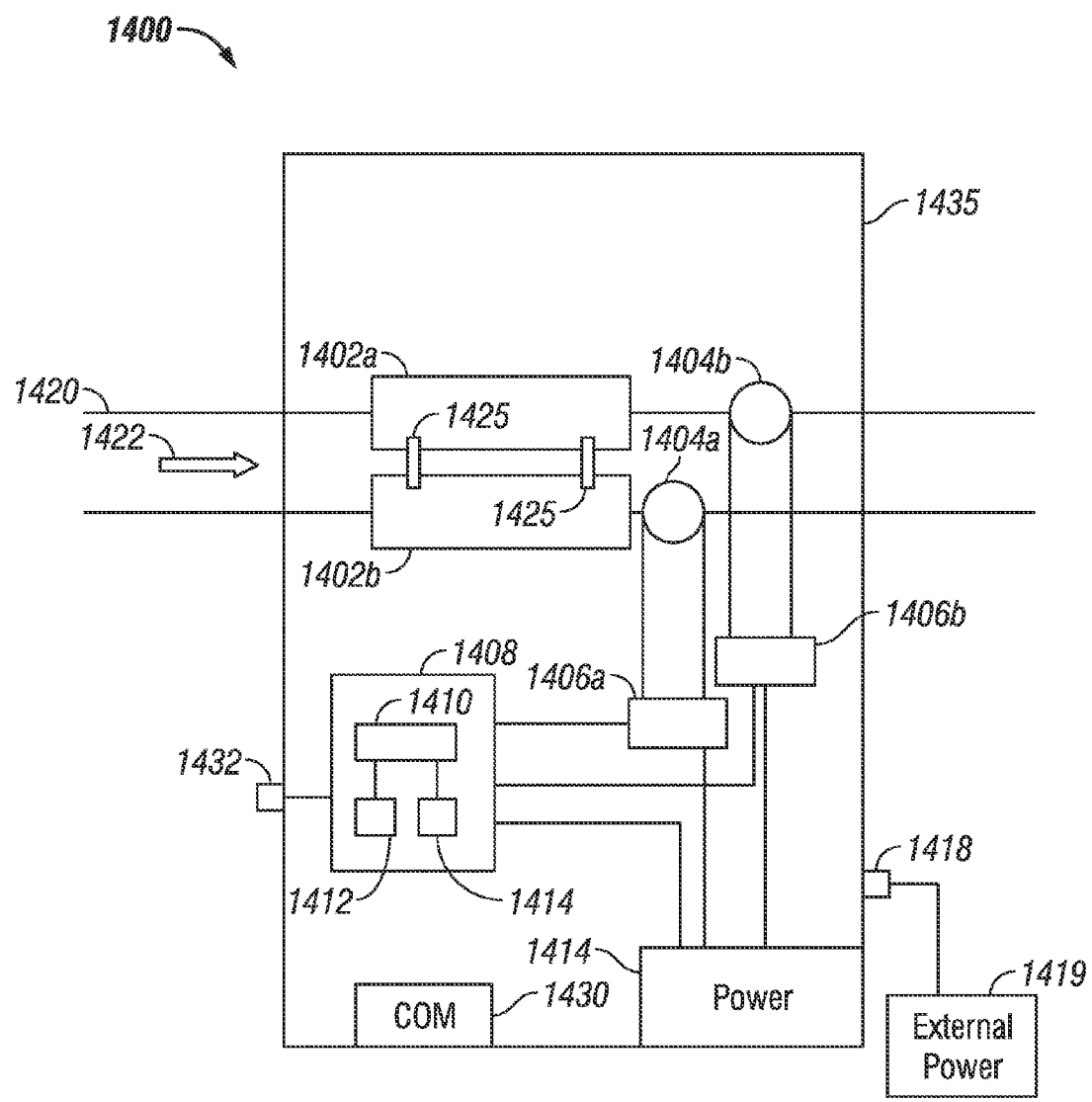
FIG. 14 shows an exemplary attachable flowmeter apparatus of the present disclosure for estimating a parameter of a fluid flowing in a tubular.

FIG. 14 shows an exemplary attachable flowmeter apparatus 1400 of the present disclosure for estimating a parameter of a fluid flowing in a tubular. In one embodiment, the exemplary attachable flowmeter 1400 is coupled to a tubular 1420 having a fluid 1422 flowing therein, such as a production tubular. The exemplary flowmeter 1400 is typically removably secured to the tubular at a non-metallic section of the tubular, such as a fiberglass portion. Thus, the flowmeter may be attached, removed and reattached to the tubular at various locations. The flowmeter may be secured to the tubular using various exemplary methods discussed below.

The exemplary flowmeter 1400 includes one or more permanent magnets 1402a and 1402b configured to induce a primary magnetic field in the fluid 1422 flowing in the tubular 1420 in order to align nuclei of the fluid along a direction of the primary magnetic field. The one or more permanent magnets may be coupled to and removable from the tubular. The one or more permanent magnets may therefore be coupled to the tubular at multiple locations of the tubular, for example, to estimate fluid parameters at various locations of the tubular. Various securing devices 1425 for securing the permanent magnets to the tubular may be used, including straps, buckles, screws, bolts, hinges, etc. In one embodiment the one or more permanent magnets are secured to each other to envelop a section of the tubular, thereby securing the magnets to the tubular. In one embodiment, the one or more permanent magnets 1402a and 1402b are coupled to a housing 1435. In this embodiment, the housing 1435 may be secured to the tubular using suitable securing methods, such as including straps, buckles, screws, bolts, hinges, etc. The housing may include two halves which, when secured to each other, envelop a portion of the tubular to thereby secure the housing 1435 to the tubular 1420. In an exemplary embodiment, the one or more permanent magnets are arranged within the housing such that securing the housing at the tubular arranges the one or more permanent magnets of the housing at the tubular to induce the primary magnetic field in the fluid for operation of the flowmeter.

One or more coils 1404a and 1404b are configured to deliver an excitation pulse to the nuclei of the fluid aligned along the primary magnetic field. In one embodiment, the one or more coils 1404a and 1404b are transmitter and receiver coils respectively. In one embodiment, the transmitter coil 1404a transmits electromagnetic energy in the form of an excitation pulse at an energy level suitable for exciting nuclear magnetic resonance of the nuclei of the fluid. In one embodiment, the excitation pulse is a radio frequency pulse. The frequency of the excitation may induce nuclear magnetic resonance of hydrogen (H1) and/or carbon (C13). However, the excitation pulse can be tuned to any suitable frequency. The direction of the magnetic field induced by the excitation pulse is typically substantially perpendicular to the direction of the primary magnetic field in the tubular but may be in any direction. The receiver coil 1404b may receive signals from the fluid responsive to the excitation pulses transmitted by the transmitter coil 1404a. The number of transmitter and/or receiver coils is not meant as a limitation to the present disclosure. In one embodiment, a single coil may be used as transmitter and receiver. The one or more coils 1404a and 1404b may also be attached to the housing 1435. Typically, the coils are arranged within the housing such that securing the housing to the tubular arranges the one or more coils in a position suitable for inducing excitation pulses in a direction substantially perpendicular to the direction of the primary magnetic field.

Coils 1404a and 1404b may be controlled via various transmitter and receiver electronics units 1406a and 1406b configured to induce excitation pulses in the transmitter and/or to detect signals induced at the receiver. Control unit 1408 is coupled to electronics units 1406a and 1406b and controls operation of the electronic units 1406a and 1406b. The control unit 1408 further receives various signals from the receiver electronics unit 1406b and in one aspect estimates a parameter of the fluid from the received signals. The control unit 1408 may include at least one processor 1410, various programs 1412 stored on a computer-readable medium accessible to the processor and at least one storage medium 1414 for storing an estimated parameter of interest of the fluid, among other things. These parameters of interest may include a spin-lattice relaxation rate of the nuclei, a spin-spin relaxation rate of the nuclei, a volume of the fluid in the tubular, a velocity of fluid in the tubular, a volumetric flow rate, a phase volume fraction of a multi-phase fluid in the tubular including phase volume fractions of oil, gas and water phases, viscosity, water cut, and an emulsion stability parameter, among others. In one embodiment, the electronics units 1406a and 1406b are coupled to the housing 1435. The control unit 1408 may also be coupled to housing 1435.

Exemplary housing 1435 may further include a power supply 1414 for powering the electronic components of the flowmeter. In another embodiment, the housing 1435 may include a power input port 1418 configured to connect the electronic equipment of the housing to an external power supply 1419, which may include a power supply of an electrical submersible pump or a booster pump, for example. The housing may further include a communication device 1430 for transmitting and receiving instructions to and from a remote unit as well as for transmitting an estimated property and/or other data to the remote unit. Alternatively, the housing may include a communication port 1432 at which an external memory device can be inserted and removed for data transfer and transport of data to and from a remote location.

Figure 15:
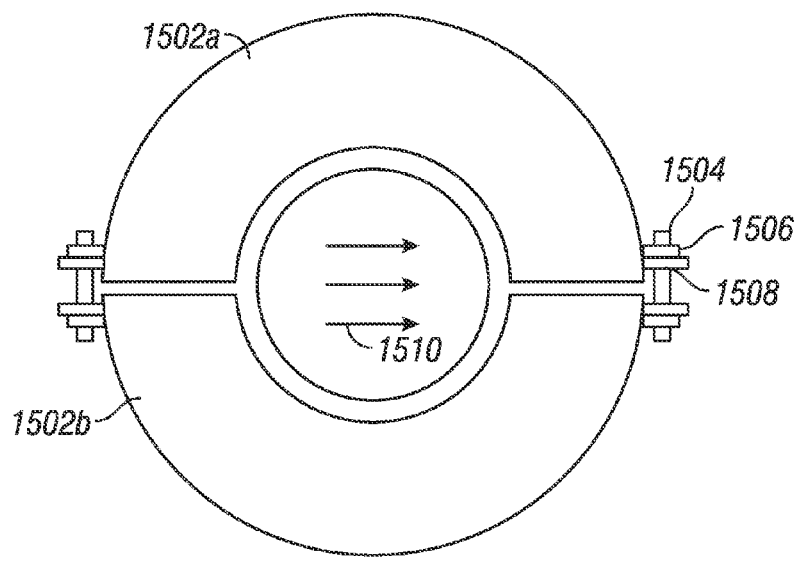
FIG. 15 shows a cross-sectional view of exemplary permanent magnets of the present disclosure attachable to a tubular to provide a magnetic field in the tubular.

FIG. 15 shows a cross-sectional view of exemplary permanent magnets of the present disclosure attachable to a tubular to provide a magnetic field in a tubular. The permanent magnets may include segmented magnets which may coupled together to provide a substantially uniform magnetic field in the tubular. In a particular embodiment, the one or more permanent magnets include C-shaped magnets 1502a and 1502b. The permanent magnets may be assembled to substantially form an annulus, wherein the radius of the inner diameter of the annulus is substantially the same as the outer diameter of the tubular. The permanents magnets may be secured to the tubular using any suitable securing device, such as one or more clamps, screws, buckles, hinges, etc. The exemplary securing device of FIG. 15 includes a socket 1508 secured to one of the permanent magnets. Another socket is secured to the other of the permanent magnets. Bolt 1504 is inserted through both sockets and secured by nuts 1506, thereby securing the permanent magnets to the tubular. In various embodiments, the magnetic field provided by the one or more magnets is oriented transverse to the longitudinal axis of the tubular, as shown by magnetic field lines 1510.

In one embodiment, the attachable flowmeter is coupled to the tubular at a surface location. In another embodiment, the attachable flowmeter is coupled to the tubular at a subsea location. At the subsea location, a machine may be controlled used to secure the various components of the flowmeter to the tubular, such as at least one of the one or more permanent magnets, the transmitter and/or receiver coils, and or the housing of the flowmeter. The controlled machine may be configured to insert and/or remove a memory device into the flowmeter to receive data from the flowmeter including the various estimated fluid parameters disclosed herein.

Figure 16:
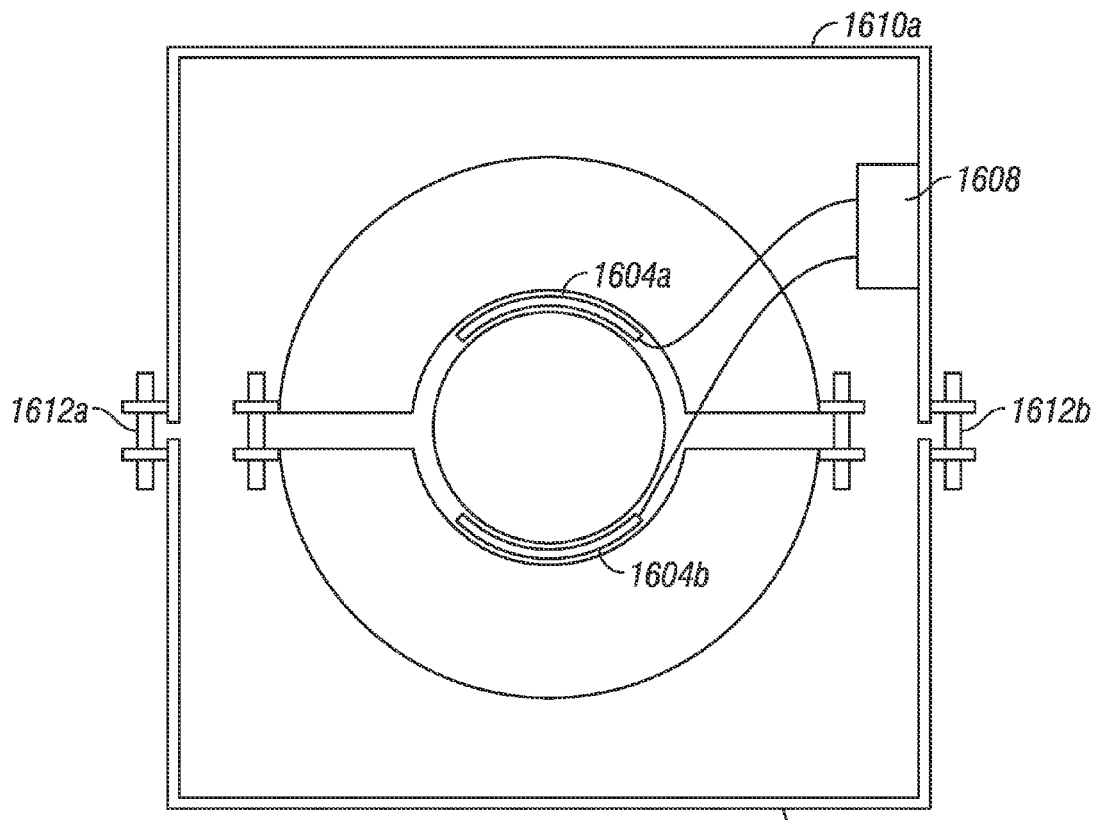
FIG. 16 shows a cross-sectional view of an exemplary an exemplary housing of the present disclosure.

FIG. 16 shows a cross-sectional view of an exemplary housing of the present disclosure. The housing includes two housing halves 1610a and 1610b which can be coupled to each other to secure the housing to the tubular. Control unit and electronics units, referred to generally as 1608, may be secured within a first housing half 1610a and coils 1604a and 1604b may be secured to respective housing halves 1610a and 1610b. The housing may be assembled using any of the exemplary securing devices 1612a and 1612b. In one embodiment, the securing devices 1612a and 1612b may include the bolt-socket devices discussed with respect to FIG. 15.

Figure 17:
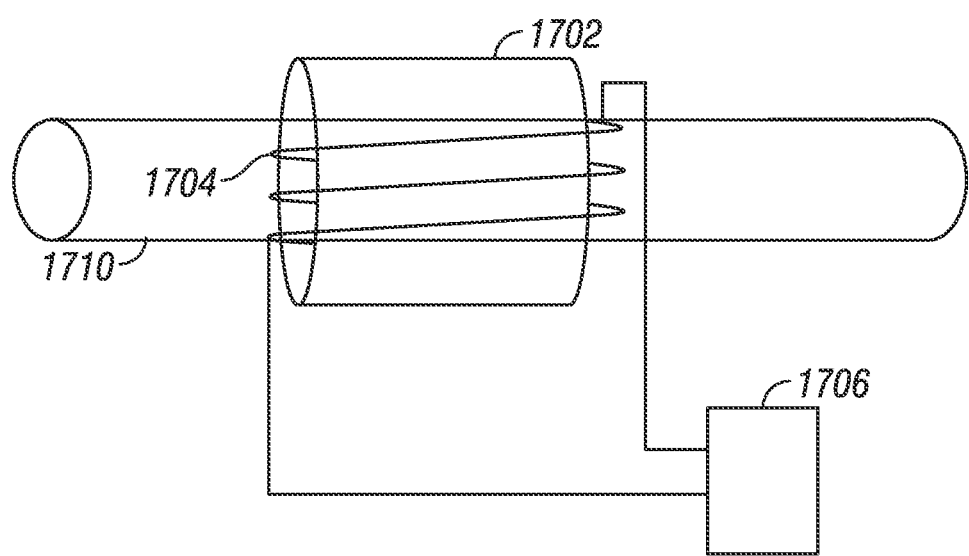
FIG. 17 shows an exemplary coil for providing a secondary polarization field in another embodiment of the present disclosure.

FIG. 17 shows an exemplary coil for providing a secondary polarization field in another embodiment of the present disclosure. Exemplary permanent magnet 1702 induces a primary magnetic field in the fluid flowing in tubular 1710. A current flowing through secondary coil 1704 induces a secondary magnetic field in the tubular. The induced secondary magnetic field may be superimposed with the primary magnetic field of the permanent magnets to either increase or reduce the total magnetic field in the fluid flowing in the tubular. In one embodiment, the induced secondary magnetic field is selected to increase the total magnetic field in the fluid to enable nuclear magnetic resonance testing at selected field strengths, or to increase a signal to noise ratio of signals responsive to an excitation pulse. In another embodiment, the induced magnetic field is selected to reduce the total magnetic field to substantially cancel the primary magnetic field within the fluid in the tubular. While a non-zero magnetic field is present in the tubular, some particles may become magnetically attached to the sides of the tubular. Substantially reducing the total magnetic field within the tubular to zero allows magnetically-attached particles to be removed or washed away, thereby preventing particle build up at the flowmeter. One skilled in the art will recognize that the strength and direction of the secondary magnetic field is related to the amount and direction, respectively, of current flowing in the secondary coil 1704. In one embodiment, the current may be controlled using an exemplary control unit 1706. In the exemplary embodiment of FIG. 17, loops of the secondary coil 1704 are oriented to provide the secondary magnetic field in a transverse direction that is either parallel or anti-parallel to the primary magnetic field. In one embodiment, the exemplary permanent magnet may include two C-shaped magnets, as discussed with respect to FIG. 15. The secondary coil 1704 may include two coils, each wrapped longitudinally around one of the C-shaped magnets. In another embodiment, for a primary magnetic field oriented along the axis of the tubular, the secondary coil may be wrapped around the circumference of the permanent magnet 1702 to provide a secondary magnetic field that can be parallel or anti-parallel to the axis of the tubular.

Therefore, in one aspect the present disclosure provides an apparatus for estimating a parameter of a fluid flowing in a tubular, including: a source of a primary magnetic field coupled to the tubular and configured to induce the primary magnetic field in the fluid to align nuclei of the fluid in the tubular along the primary magnetic field; a transmitter configured to transmit an excitation signal into the fluid; a receiver configured to detect a signal from the aligned nuclei responsive to the excitation signal; and a processor configured to estimate the parameter of the fluid from the detected signal. The source of the primary magnetic field may be placed in a housing coupled to the tubular, wherein the housing may include at least one of: (a) the transmitter coil; (b) the receiver coil; (c) the processor; (d) a communication device configured to communicate data to a remote device; (e) a communication port; (f) a power unit; and (g) a power input port. In one embodiment, the source of the primary magnetic field includes two permanent magnets coupled to the tubular at radially opposed positions. A coil may be used to induce a secondary magnetic field to perform an operation selected from a group consisting of: (i) enhance the strength of the primary magnetic field in the tubular; and (ii) substantially cancel the primary magnetic field in the tubular. The secondary magnetic field typically substantially cancels the primary magnetic field in the tubular to reduce particle build-up in the tubular. A power source may supply power to the housing that may be at least one of: (i) a power supply of an electrical submersible pump; and (ii) a power supply of a booster pump. The source of the primary magnetic field is removable from the tubular.

In another aspect, the present disclosure provides a method of estimating a parameter of a fluid flowing in a tubular, including: coupling a source of a primary magnetic field to the tubular to induce the primary magnetic field in the fluid to align nuclei of the fluid in the tubular along the primary magnetic field; transmitting an excitation signal into the flowing fluid; detecting a signal from the aligned nuclei responsive to the excitation signal; and estimating the parameter of the fluid from the detected response signal. A housing including the source of the primary magnetic field may be coupled to the tubular. The housing may further includes at least one of: (a) a transmitter coil for transmitting the excitation signal; (b) a receiver coil for detecting the response signal; (c) a processor for estimating the parameter of the fluid from the detected response signal; (d) a communication device for communicating the estimated parameter to a remote device; (e) a communication port; (f) a power unit; and (g) a power input port. The source of the primary magnetic field may include two permanent magnets configured to couple to the tubular at radially opposed positions of the tubular. In one embodiment, a secondary magnetic field induced with respect to the primary magnetic field to either enhance the strength of the primary magnetic field in the tubular or substantially cancel the primary magnetic field in the tubular. The secondary magnetic field may substantially cancel the primary magnetic field in the tubular in order to reduce particle build-up in the tubular. Power may be supplied to the housing from a power supply of one of: (i) an electrical submersible pump; and (ii) a booster pump. The primary magnetic source may be removable from the tubular.

In yet another aspect, the present disclosure provides a device for estimating a parameter of a fluid flowing in a tubular, including a first permanent magnet configured to couple to the tubular to induce a primary magnetic field in the fluid to align nuclei of the fluid along a direction of the primary magnetic field for estimating the parameter of the fluid. The device may further include a transmitter configured to transmit an excitation signal into the fluid; a receiver configured to detect a signal from the aligned nuclei responsive to the excitation signal; and a processor configured to estimate the parameter of the fluid from the detected signal. A coil of the device may be configured to induce a secondary magnetic field to do one of: (i) enhance the strength of the primary magnetic field in the tubular; and (ii) substantially cancel the primary magnetic field in the tubular. The device may include a second permanent magnet, wherein the first permanent magnet and second permanent magnet are C-shaped magnets.

While the foregoing disclosure is directed to the preferred embodiments of the disclosure, various modifications will be apparent to those skilled in the art. It is intended that all variations within the scope and spirit of the appended claims be embraced by the foregoing disclosure.

What is claimed is:

1. An apparatus for estimating a parameter of a fluid flowing in a tubular, comprising:
    a pair of magnets configured to removably secure to each other using a first securing device to envelop a portion of the tubular, wherein the pair of magnets provide a primary magnetic field in the fluid to align nuclei of the fluid in the tubular along the primary magnetic field;
    a transmitter coil configured to transmit an excitation signal into the fluid;
    a receiver coil configured to detect a signal from the aligned nuclei responsive to the excitation signal;
    a processor configured to estimate the parameter of the fluid from the detected signal;
    a housing that includes two housing halves configured to removably secure to each other using a second securing device to surround the portion of the tubular, the pair of magnets, the transmitter coil, the receiver coil and the processor, wherein the processor is secured to one of the housing halves.

2. The apparatus of claim 1 wherein the pair of magnets and the housing are configured to removably secure to the tubular at the more than one location of the tubular.

3. The apparatus of claim 2, wherein the housing further includes at least one of: (a) the transmitter coil; (b) the receiver coil; (c) the processor; (d) a communication device configured to communicate data to a remote device; (e) a communication port; (f) a power unit; and (g) a power input port.

4. The apparatus of claim 1, wherein the pair of magnets are configured to removably secure to each other at radially opposed positions of the tubular.

5. The apparatus of claim 1 further comprising a secondary coil configured to induce a secondary magnetic field to perform an operation selected from a group consisting of: (i) enhancing the strength of the primary magnetic field in the tubular; and (ii) substantially cancelling the primary magnetic field in the tubular.

6. The apparatus of claim 5, wherein the secondary magnetic field substantially cancels the primary magnetic field in the tubular to reduce particle build-up in the tubular.

7. The apparatus of claim 1 further comprising a power supply configured to supply power to the housing that is the power supply for one of: (i) an electrical submersible pump; and (ii) a booster pump.

8. The apparatus of claim 1, wherein at least one of the first securing device and the second securing device includes one of: a clamp; a screw; a buckle; and a hinge.

9. A method of estimating a parameter of a fluid flowing in a tubular, comprising:
    securing a pair of magnets to each other using a first securing device to secure the pair of magnets to the tubular, wherein the pair of magnets induce a primary magnetic field in the fluid to align nuclei of the fluid in the tubular along the primary magnetic field, wherein the pair of magnets are removably securable to the tubular at more than one location of the tubular;
    removably coupling two housing halves of a housing to each other using a second securing device to removably secure the housing to the tubular to surround the pair of magnets, a transmitter coil, a receiver coil and a processor, wherein the processor is secured to one of the housing halves;
    transmitting an excitation signal from the transmitter coil into the flowing fluid;
    detecting a response signal at the receiver coil from the aligned nuclei responsive to the excitation signal; and
    estimating, using the processor, the parameter of the fluid from the detected response signal.

10. The method of claim 9, wherein the pair of magnets and the housing are removably securable to the tubular at more than one location of the tubular.

11. The method of claim 10, wherein the housing further includes at least one of: (a) the transmitter coil for transmitting the excitation signal; (b) the receiver coil for detecting the response signal; (c) the processor for estimating the parameter of the fluid from the detected response signal; (d) a communication device for communicating the estimated parameter to a remote device; (e) a communication port; (f) a power unit; and (g) a power input port.

12. The method of claim 9, wherein the pair of magnets comprises two permanent magnets configured to removably secure to each other at radially opposed positions of the tubular.

13. The method of claim 12 further comprising inducing a secondary magnetic field with respect to the primary magnetic field to perform an operation selected from a group consisting of: (i) enhancing the strength of the primary magnetic field in the tubular; and (ii) substantially cancelling the primary magnetic field in the tubular.

14. The method of claim 13 further comprising substantially cancelling the primary magnetic field in the tubular to reduce particle build-up in the tubular.

15. The method of claim 9 further comprising supplying power to the housing from a power supply of one of: (i) an electrical submersible pump; and (ii) a booster pump.

16. A device for estimating a parameter of a fluid flowing in a tubular, comprising:
- a pair of permanent magnets configured to removably secure to each other using a first securing device to couple the pair of permanent magnets to the tubular, wherein the pair of permanent magnets induces a primary magnetic field in the fluid to align nuclei of the fluid along a direction of the primary magnetic field for estimating the parameter of the fluid;
- a transmitter coil;
- a receiver coil;
- a processor; and
- a housing comprising two housing halves configured to removably secure to each other using a second securing device to secure the housing to the tubular and to surround the pair of permanent magnets, the transmitter coil, the receiver coil and the processor, wherein the processor is coupled to one of the housing halves.

17. The device of claim 16, wherein the processor is configured to estimate the parameter of the fluid from a detected signal.

18. The device of claim 17, further comprising a secondary coil configured to induce a secondary magnetic field to do one of: (i) enhancing the strength of the primary magnetic field in the tubular; and (ii) substantially cancelling the primary magnetic field in the tubular.

19. The device of claim 16, wherein the pair of permanent magnets includes a pair of C-shaped magnets.

* * * * *